United States Patent [19]

Swallow

[11] 4,352,685
[45] Oct. 5, 1982

[54] PROCESS FOR REMOVING NITROGEN FROM NATURAL GAS

[75] Inventor: Brian R. Swallow, Grand Island, N.Y.

[73] Assignee: Union Carbide Corporation, Danbury, Conn.

[21] Appl. No.: 276,899

[22] Filed: Jun. 24, 1981

[51] Int. Cl.³ .............................................. F25J 3/02
[52] U.S. Cl. ........................................... 62/28; 62/24
[58] Field of Search ........................... 62/24, 28, 29, 38

[56] References Cited

U.S. PATENT DOCUMENTS 3,271,099 4/1975 Forg et al. ............................. 62/28
3,874,184 4/1975 Harper et al. .......................... 62/28

OTHER PUBLICATIONS

"Nitrogen Removal," Hydrocarbon Processing, Apr. 1975, p. 99.
Harris, "Design Considerations For Nitrogen Rejection Plants," Apr. 17, 1980.

Primary Examiner—Norman Yudkoff
Attorney, Agent, or Firm—Stanley Ktorides

[57] ABSTRACT

A process which effectively removes nitrogen from natural gas over a wide range of nitrogen concentrations and wherein the natural gas may also contain high concentrations of heavy hydrocarbons. The process is especially advantageous for the purification of a natural gas stream recovered from a petroleum field where nitrogen injection is employed as an enhanced recovery technique.

18 Claims, 1 Drawing Figure

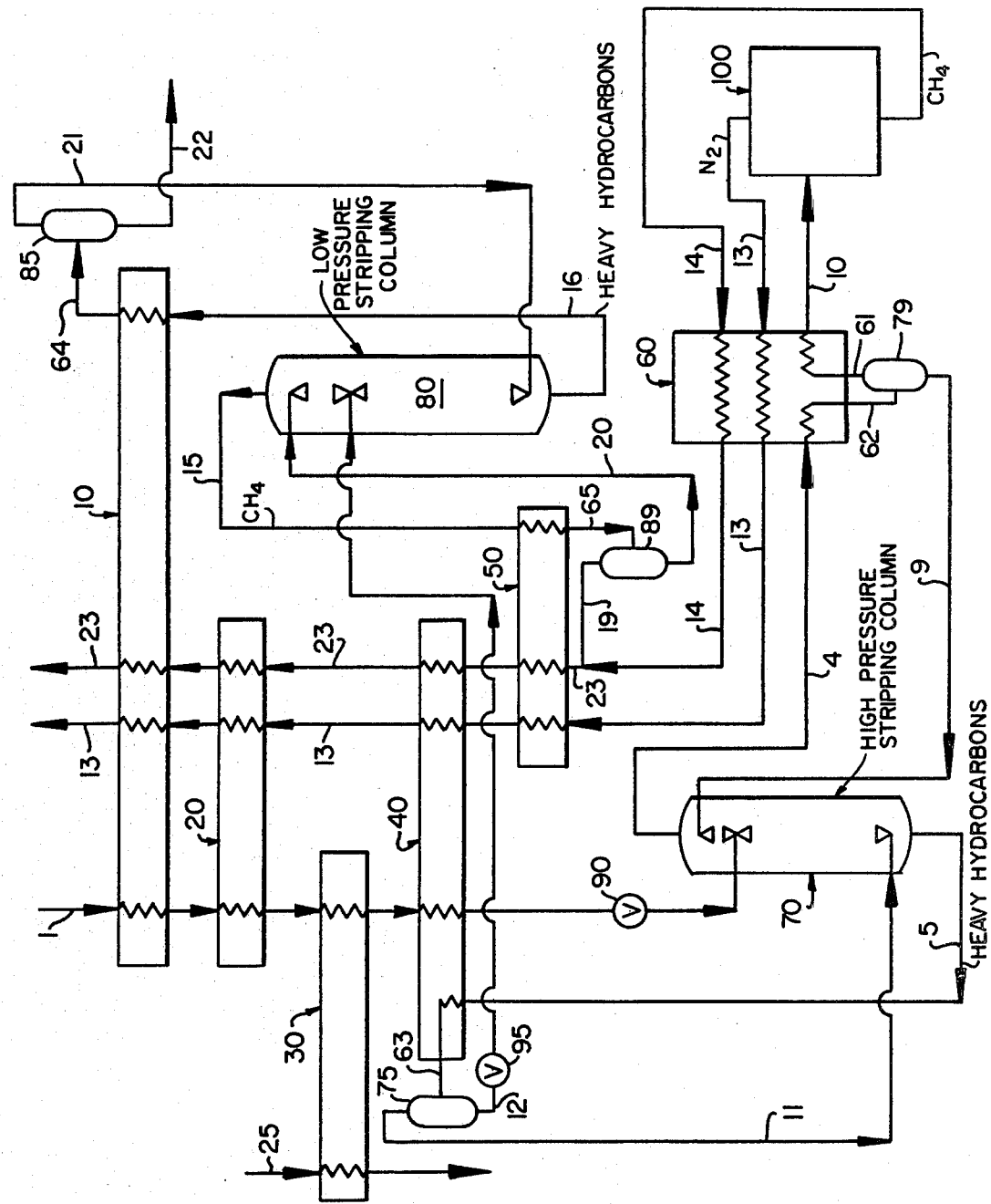

PROCESS FOR REMOVING NITROGEN FROM NATURAL GAS

BACKGROUND OF INVENTION

This invention is a process for removing nitrogen from natural gas, and is especially useful when the nitrogen content of the natural gas stream varies considerably over time, and when the natural gas stream also contains a sizeable concentration of heavy hydrocarbons.

Recovery of high quality natural gas is becoming increasingly important as the price of energy continues to rise. Furthermore, natural gas usage tends to minimize the quantity of pollutants produced for a given amount of energy generated when compared to certain other commonly used means of energy generation.

One problem often encountered in natural gas recovery is nitrogen contamination. Natural gas which has significant amounts of nitrogen may not meet minimum heating value specifications, reduces pipeline capacities and requires additional compression horsepower and fuel consumption. Further, nitrogen in natural gas may lead to the formation of undesired nitrogen oxides when the natural gas is burned. Nitrogen removal from natural gas has therefore attained increased importance.

In many cases, successful recovery of the natural gas requires the use of an enhanced recovery technique. One such often used technique involves the injection into the well of a fluid which will not support combustion; an often used fluid for this technique is nitrogen due to its relatively low cost compared to argon, helium and the like. However, the use of this technique increases the level of nitrogen contaminant in the natural gas above the naturally-occurring nitrogen concentration.

Nitrogen injection for enhanced recovery introduces a further problem because the nitrogen concentration in the natural gas does not remain constant over the life of the recovery operation. During the first few years that enhanced recovery with nitrogen injection is employed, the nitrogen concentration in the natural gas may remain at about the naturally-occurring level, increasing thereafter, for example, by about 5 percent after 4 years, by about 15 percent after 8 years, by about 25 percent after 10 years and by about 50 percent after 16 years.

In response to the problem of nitrogen contamination of natural gas, several methods of separating the nitrogen from the natural gas have been developed. A commonly used method employs a dual pressure double distillation column; this type of arrangement is often used in the fractionation of air into oxygen and nitrogen. However, this method is generally limited to applications where the nitrogen concentration of the natural gas is greater than about 20 to 25 percent. Where the nitrogen concentration is lower than 20 to 25 percent, the quantity of reflux liquid that can be generated in the high pressure column decreases to the extent that proper fractionation cannot be conducted in the low pressure column.

Generally, prior methods of cleaning natural gas of nitrogen at such low nitrogen concentration have been designed for natural gas having low concentrations of heavy hydrocarbons and/or a relatively unchanging nitrogen concentration in the natural gas.

The problem of a changing nitrogen concentration in the natural gas further complicates the economics of recovery. As shown, for example, in "Design Considerations For Nitrogen Rejection Plants," R. A. Harris, Apr. 17, 1980, The Randall Corp., Houston, Tex., the specific nitrogen removal process employed will be dictated by the nitrogen concentration. A nitrogen concentration of from 15 to 25 percent will require one type of process, a nitrogen concentration of from 25 to 40 percent will require another, a nitrogen concentration of 40 to 50 percent still another process, and a concentration greater than about 50 percent yet another process. The alternative, i.e., the use of only one process as the nitrogen concentration in the natural gas varies, will result in severe operating inefficiencies.

OBJECTS

Accordingly, it is an object of this invention to provide an improved process for removing nitrogen from natural gas.

It is another object of this invention to provide an improved process for removing nitrogen from natural gas wherein the nitrogen concentration in the natural gas may vary from the naturally-occurring concentration to as high as 50 percent or more.

It is another object of this invention to provide an improved process for removing nitrogen from natural gas wherein the natural gas also contains a high concentration of heavy hydrocarbons.

SUMMARY OF THE INVENTION

The above and other objects of this invention which will become apparent to one skilled in the art are achieved by:

A process for separating nitrogen from natural gas comprising:

(1) introducing an at least partially condensed nitrogen-containing natural gas feed stream, which is essentially free of water and carbon dioxide and is at a pressure of at least 400 psia, to a first stripping column wherein the stream is separated by rectification into a nitrogen-methane gas stream A, and a heavy hydrocarbon-methane liquid stream B;

(2) partially condensing stream A to produce a nitrogen-methane gas stream C and a liquid stream D;

(3) introducing stream D to said first stripping column;

(4) introducing stream C to a nitrogen-methane separation zone wherein the stream is separated into a nitrogen stream E and a methane stream F;

(5) partially vaporizing stream B to produce a gas stream G and a heavy hydrocarbon-enriched liquid stream H;

(6) introducing stream G to said first stripping column as vapor reflux;

(7) introducing stream H to a second stripping column wherein it is separated by rectification into a methane-rich stream I and a liquid stream J;

(8) partially condensing stream I to produce a methane gas stream K and a liquid stream L;

(9) introducing stream L to said second stripping column;

(10) partially vaporizing stream J to produce a gas stream M and a heavy hydrocarbon liquid stream N;

(11) introducing stream M to said second stripping column as vapor reflux; and

(12) recovering stream F and stream K as product methane.

The term, natural gas, is used to mean a fluid which has a significant methane content.

The term, heavy hydrocarbon, is used to mean a hydrocarbon having two or more carbon atoms.

The term, sizeable concentration of heavy hydrocarbons, is used to mean a fluid having a heavy hydrocarbon to methane mole ratio of greater than 0.1.

The term, column, is used to mean a distillation column, i.e., a contacting column wherein liquid and vapor phases are countercurrently contacted to effect separation of a fluid mixture, as for example, by contacting of the vapor and liquid phases on a series of vertically spaced trays or plates mounted within the column or alternatively, on packing elements with which the column is filled. For an expanded discussion see the Chemical Engineers' Handbook, Fifth Edition, edited by R. H. Perry and C. H. Chilton, McGraw-Hill Book Company, New York, Section 13, "Distillation" B. D. Smith et al., page 13-3, *The Continuation Distillation Process.*

The term, double distillation column, is used to mean a higher pressure distillation column having its upper end in heat exchange relation with the lower end of a low pressure distillation column. Examples of a double distillation column appear in Ruheman's "The Separation of Gases" University Press, 1949.

The term, stripping column, is used to mean that part or zone of a distillation column which is below the feed stage. For an expanded discussion of a stripping column, see *Design of Equilibrium Stage Processes,* B. D. Smith, McGraw-Hill Book Company, New York, 1963 pp. 143-146.

BRIEF DESCRIPTION OF THE DRAWING

FIG. 1 is a schematic representation of a preferred embodiment of the process of this invention.

DESCRIPTION OF THE INVENTION

The process of this invention will be described in detail with reference to FIG. 1.

A nitrogen-containing natural gas stream 1, generally at a pressure above 600 psia and preferably at about 1000 psia or more, which has been treated to remove condensible contaminants such as water and carbon dioxide, for example, by molecular sieve adsorption, is cooled sequentially in heat exchangers 10, 20, 30 and 40 in order to partially condense the less volatile fraction of the feed stream. The pressure recited above for the incoming gas stream is generally in the pressure range at which natural gas is recovered from a well; however, the pressure of the incoming natural gas stream introduced to the first stripping column may be as low as 400 psia. Generally, the nitrogen concentration of the gas stream is from about 15 to 60 percent.

The cooled and partially condensed stream is then throttled through valve 90 to a pressure below the critical pressure of the gas mixture. This step produces refrigeration of the separation plant via the well known Joule-Thompson expansion. As can be appreciated, the higher the pressure of the incoming natural gas stream, the more Joule-Thompson cooling is obtained, and thus the more efficient is the overall separation process.

As indicated above, the gas mixture must be reduced to below its critical pressure before it is introduced to the stripping column. As is well known, at pressure above critical, two phases will not simultaneously exist and thus separation is impossible. The critical pressure of methane is 673 psia and that of nitrogen is 492 psia. The critical pressure of the nitrogen-methane gas mixture will primarily depend upon the specific concentrations of these components.

Generally, the requirement that column feed be below the critical pressure is not dwelled upon since feed is generally at a low pressure initially. It is mentioned here because the feed, generally from a gas well, will generally be at a relatively high pressure. In fact, as previously mentioned, it is preferable that the feed be at 1000 psia or more.

Since the stream is introduced to a stripping column, the feed must be at least partially condensed; this requirement is well known to those skilled in the art and is further explained in the Smith reference mentioned earlier.

The throttled stream is then fed to a stripping column 70 where it is separated by rectification into a gas stream 4 which comprises primarily nitrogen and methane and a liquid stream 5 which comprises primarily heavy hydrocarbons and methane. A stripping column is employed in order to avoid the high refrigeration required to generate adequate reflux flow. At the higher nitrogen concentrations, this refrigeration requirement would be excessive. It has been unexpectedly found that a stripping column will provide the necessary degree of separation when the nitrogen concentration of the incoming natural gas stream is relatively low. Thus, by the use of the process of this invention employing stripping columns, one can now carry out a nitrogen separation which is efficient from both an economic and technical viewpoint at either relatively high or relatively low nitrogen concentrations in the feed.

The nitrogen-methane gas stream 4 is then partially condensed in heat exchanger 60 and passed 62 to phase separato 79 where it is separated into a nitrogen-methane gas stream 61 and a liquid stream 9 which is returned to stripping column 70. The gas stream 61 is further cooled in heat exchanger 60 and the resulting stream 10 is fed to a nitrogen-methane separation zone 100.

The nitrogen-methane separation zone 100 is shown in FIG. 1 in block schematic form. Preferably the nitrogen-methane separation zone is a dual pressure double column which is commonly employed to separate gases such as the production of oxygen from air. In a double distillation column the high pressure column partially separates the nitrogen-methane mixture generating a nitrogen liquid stream which is employed as reflux for the low pressure column. The methane-containing liquid from the kettle of the high pressure column, still containing a significant amount of nitrogen, is the feed for the low pressure column wherein it is separated into a high purity overhead nitrogen stream and a high purity methane product recovered from the kettle. The heat necessary to produce vapor reflux for the low pressure column is obtained from the condensing nitrogen gas in the overhead of the high pressure column. As noted above, double distillation columns are well known to those skilled in the art and no further discussion is necessary here.

Stream 10 will generally have a nitrogen concentration of above about 20 percent and it is preferably above about 25 percent. The double distillation column separates the feed into a nitrogen stream 13 and a methane product stream 14. FIG. 1 shows a preferred embodiment of the process of this invention wherein the nitrogen and/or methane streams from the nitrogen-methane separation zone 100 are employed to absorb heat in heat exchanger 60. In the most preferred embodiment of the process of this invention the gas stream 4 is partially condensed in heat exchanger 60 solely by countercurrent heat exchange with the nitrogen and/or methane streams.

Liquid stream 5 is partially vaporized and, as shown in FIG. 1, this partial vaporization is preferably in heat exchanger 40 countercurrently against the feed stream 1. The partially vaporized stream 63 is passed to phase separator 75 where it is separated into a gas stream 11, which is returned to stripping column 70 as vapor reflux, and a heavy hydrocarbon-enriched stream 12.

As shown, both the overhead and bottom streams recovered from stripping column 70 are respectively cooled and warmed preferably by countercurrent heat exchange and preferably against internal streams. Since both of these streams are multi-component mixtures countercurrent heat exchange is thermodynamically more efficient than concurrent heat exchange. Further, by providing only a partial condensation or vaporization, an additional equilibrium stage of separation is added to each end of stripping column 70. As a result, a significant quantity of nitrogen present in the kettle liquid is effectively prevented from contaminating the ultimate products recovered from the hydrocarbon-enriched liquid 12. Similarly, a sizeable fraction of the heavy hydrocarbons in stream 4 are returned to the stripping column in stream 9. This allows the more efficient purification of a natural gas stream containing a changing nitrogen concentration and with a sizeable heavy hydrocarbon concentration. Thus, the process of this invention can effectively separate nitrogen from natural gas at a variety of nitrogen concentrations in the feed and when the natural gas also contains a significant concentration of heavy hydrocarbons.

Continuing with the description of the process of this invention and referring again to FIG. 1, heavy hydrocarbon-enriched stream 12 is throttled through valve 95 in order to effect more Joule-Thompson cooling; thus, the bulk of the refrigeration required is provided from internal sources. At this point the pressure of the stream is generally between 300 to 400 psia.

The stream is then fed to stripping column 80 where it is separated by rectification into a methane-rich stream 15 and a liquid stream 16 which contains a significant concentration of heavy hydrocarbons. Stream 16 is partially vaporized preferably in heat exchanger 10 by countercurrent heat exchange with the feed stream 1. The partially vaporized stream 64 is then fed to phase separator 85 where it is separated into a liquid heavy hydrocarbon stream 22 and a gas stream 21 which is returned to stripping column 80 as vapor reflux. The heavy hydrocarbon stream 22 may be recovered as product liquid petroleum gas or LPG.

The methane stream 15 is partially condensed preferably in heat exchanger 50 by countercurrent heat exchange with the nitrogen and/or methane streams from the nitrogen-methane separation zone 100. The partially condensed stream 65 is then fed to phase separator 89 where it is separated into a methane gas stream 19 and a liquid stream 20 which is returned to stripping column 80. Methane gas stream 19 is recovered as purified product methane. Preferably it is combined with methane product stream 14 from the nitrogen-methane separation zone 100 to form methane product stream 23 which is recovered as product methane. The nitrogen stream 13 from the nitrogen-methane separation zone 100 can be simply released to the atmosphere or, if desired, recovered as product nitrogen.

As previously mentioned, the incoming stream to second stripping column 80 is generally at a pressure of between 300 to 400 psia, signifying a pressure difference between the first and second stripping column. At the lower pressure, the separation in the second stripping column is better due to the higher relative volatilities of the components. However, there need not be a pressure difference between the first and second stripping columns for the process of this invention to be effective. The pressure in the second stripping column 80 can also be below 300 psia, although at such a pressure there will generally be required additional refrigeration.

By employing the two stripping columns as defined by the process of this invention, one can get two pure products, i.e., methane and heavy hydrocarbons; this cannot be done in only one column or separation zone. Further, the use of two stripping columns gives one the option of a lower pressure, thus achieving a more efficient separation.

In the embodiment shown in FIG. 1, the refrigeration necessary for the separation is supplied by external refrigerant stream 25 through heat exchanger 30. Preferably, additional refrigeration is obtained from the Joule-Thompson expansion of the feed gas as described above. Other methods of generating refrigeration include the work expansion of an appropriate internal stream and the incorporation into the process of an appropriate heat pump cycle. When the most preferred embodiment of this invention is employed, wherein heat transfer is effected through countercurrent heat exchange with appropriate internal streams, external refrigeration is required only at temperatures above about $-100°$ C. (e.g., $-50°$ C.).

Table I summarizes two runs employing the process of this invention. Column A summarizes the separation of a stream containing only 15 percent nitrogen and significant concentration of heavy hydrocarbons. Column B summarizes the separation of a stream containing 50 percent nitrogen. Percentages refer to mole percent and stream numbers correspond to those of FIG. 1. As is shown, the process of this invention effectively separates nitrogen from a natural gas stream which may also contain a high concentration of heavy hydrocarbons over a large range of nitrogen concentrations in the natural gas. The mole ratio of heavy hydrocarbon to methane in each of runs A and B was 0.22.

The process of this invention has been described in detail with reference to a specific preferred embodiment illustrated in FIG. 1. However, as can be readily appreciated, the process of this invention contemplates many other embodiments and is not limited to those embodiments specifically described and illustrated.

TABLE I

|  | A | B |
|---|---|---|
| FEED (STREAM #1) | | |
| FLOW RATE (lb mol/hr) | 100 | 100 |
| PRESSURE (psia) | 1000 | 1000 |
| NITROGEN (%) | 15.0 | 50.0 |
| METHANE (%) | 69.9 | 41.1 |
| $C_2^+$-HYDROCARBONS (%) | 15.1 | 8.9 |
| METHANE PRODUCT (STREAM #23) | | |
| FLOW RATE (lb mol/hr) | 71.5 | 42.7 |
| PRESSURE (psia) | 275 | 160 |
| NITROGEN (%) | 2.3 | 2.3 |
| METHANE (%) | 95.5 | 95.7 |
| $C_2^+$-HYDROCARBONS (%) | 2.2 | 2.0 |
| LPG PRODUCT STREAM (#22) | | |
| FLOW RATE (lb mol/hr) | 13.8 | 8.2 |
| PRESSURE (psia) | 300 | 300 |
| NITROGEN (%) | — | — |

TABLE I-continued

|  | A | B |
|---|---|---|
| METHANE (%) | 1.5 | 1.5 |
| $C_2^+$-HYDROCARBONS (%) | 98.5 | 98.5 |
| NITROGEN PRODUCT (STREAM #13) | | |
| FLOW RATE (lb mol/hr) | 14.7 | 49.1 |
| PRESSURE (psia) | 28 | 28 |
| NITROGEN (%) | 90.3 | 99.8 |
| METHANE (%) | 9.7 | 0.2 |
| $C_2^+$-HYDROCARBONS (%) | — | — |
| METHANE RECOVERY IN METHANE PRODUCT (%) | 97.7 | 99.4 |
| $C_2^+$-HYDROCARBON RECOVERY IN LPG PRODUCT (%) | 90.0 | 90.8 |

What is claimed is:

1. A process for separating nitrogen from natural gas comprising:
   (1) introducing an at least partially condensed nitrogen-containing natural gas feed stream which is essentially free of water and carbon dioxide and is at a pressure of at least 400 psia, to a first stripping column wherein the stream is separated by rectification into a nitrogen-methane gas stream A and a heavy hydrocarbon-methane liquid stream B;
   (2) partially condensing stream A to produce a nitrogen-methane gas stream C and a liquid stream D;
   (3) introducing stream D to said first stripping column;
   (4) introducing stream C to a nitrogen-methane separation zone wherein the stream is separated into a nitrogen stream E and a methane stream F;
   (5) partially vaporizing stream B to produce a gas stream G and a heavy hydrocarbon-enriched liquid stream H;
   (6) introducing stream G to said first stripping column as vapor reflux;
   (7) introducing stream H to a second stripping column wherein it is separated by rectification into a methane-rich stream I and a liquid stream J;
   (8) partially condensing stream I to produce a methane gas stream K and a liquid stream L;
   (9) introducing stream L to said second stripping column;
   (10) partially vaporizing stream J to produce a gas stream M and a heavy hydrocarbon liquid stream N;
   (11) introducing stream M to said second stripping column as vapor reflux; and
   (12) recovering stream F and stream K as product methane.

2. The process of claim 1 wherein streams F and K are combined into one stream before they are recovered as product methane.

3. The process of claim 1 wherein heavy hydrocarbon liquid stream N is recovered as product liquid petroleum gas.

4. The process of claim 1 wherein stream E is released to the atmosphere.

5. The process of claim 1 wherein stream E is recovered as product nitrogen.

6. The process of claim 1 wherein stream A is partially condensed by countercurrent heat exchange with stream E and/or stream F.

7. The process of claim 1 wherein stream B is partially vaporized by countercurrent heat exchange with the nitrogen-containing natural gas feed stream.

8. The process of claim 1 wherein stream I is partially condensed by countercurrent heat exchange with stream E and/or stream F.

9. The process of claim 1 wherein stream J is partially vaporized by countercurrent heat exchange with the nitrogen-containing natural gas feed stream.

10. The process of claim 1 wherein said nitrogen-methane separation zone is a double distillation column.

11. The process of claim 1 wherein the concentration of nitrogen in the nitrogen-containing natural gas feed stream is from about 15 to 60 percent.

12. The process of claim 1 wherein the nitrogen-containing natural gas feed stream additionally contains heavy hydrocarbons in a concentration such that the mole ratio of heavy hydrocarbon to methane is greater than 0.1.

13. The process of claim 1 wherein the concentration of nitrogen in stream C immediately before its introduction to the nitrogen-methane separation zone is at least 20 percent.

14. The process of claim 1 wherein the nitrogen-containing natural gas feed stream is at a pressure of at least 600 psia.

15. The process of claim 1 wherein the pressure of the nitrogen-containing natural gas feed stream is initially at or above its critical pressure and said pressure is reduced to below the critical pressure before the feed stream is introduced to the first stripping column.

16. The process of claim 15 wherein said pressure is 1000 psia or more.

17. The process of claim 1 wherein the pressure in the second stripping column is less than the pressure in the first stripping column.

18. The process of claim 1 wherein the pressure in the second stripping column is from about 300 to about 400 psia.

* * * * *